(12) United States Patent
Wenchell et al.

(10) Patent No.: US 7,811,251 B2
(45) Date of Patent: Oct. 12, 2010

(54) TROCAR ANCHOR

(75) Inventors: Thomas Wenchell, Durham, CT (US); Richard D. Gresham, Guilford, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 559 days.

(21) Appl. No.: 11/249,830

(22) Filed: Oct. 13, 2005

(65) Prior Publication Data

US 2007/0088258 A1   Apr. 19, 2007

(51) Int. Cl.
*A61M 29/00* (2006.01)
*A61M 5/178* (2006.01)

(52) U.S. Cl. .................................. 604/107; 604/164.03

(58) Field of Classification Search ......... 604/104–107, 604/288.01, 41, 42, 95.04, 164.03, 164.04
See application file for complete search history.

(56) References Cited

U.S. PATENT DOCUMENTS

| | | | |
|---|---|---|---|
| 1,870,942 A | 8/1932 | Beatty | |
| 2,854,983 A | 10/1958 | Baskin | |
| 3,108,595 A | 10/1963 | Overment | |
| 3,312,215 A | 4/1967 | Silber | |
| 3,397,699 A | 8/1968 | Kohl | |
| 3,487,837 A * | 1/1970 | Petersen | 604/180 |
| 3,716,051 A | 2/1973 | Fischer | |
| 3,779,239 A | 12/1973 | Fischer et al. | |
| 3,915,171 A | 10/1975 | Shermeta | |
| 3,961,632 A | 6/1976 | Moossun | |
| 4,224,929 A | 9/1980 | Furihata | |
| 4,409,974 A | 10/1983 | Freedland | |
| 4,430,076 A | 2/1984 | Harris | |
| 4,453,539 A | 6/1984 | Raftopoulos et al. | |
| 4,496,345 A | 1/1985 | Hasson | |
| 4,503,843 A | 3/1985 | Boebel | |
| 4,608,965 A | 9/1986 | Anspach, Jr. et al. | |
| 4,617,933 A | 10/1986 | Hasson | |

(Continued)

FOREIGN PATENT DOCUMENTS

DE   2411226   9/1974

(Continued)

OTHER PUBLICATIONS

European Search Report for EP 06021336, date of completion is Jan. 17, 2007 (3 pgs).

(Continued)

*Primary Examiner*—Kevin C Sirmons
*Assistant Examiner*—Bradley J Osinski

(57) ABSTRACT

Apparatus and methods for providing access to a body cavity without substantial loss of inflation gas therein. The apparatus includes an access assembly that has a tubular member having a proximal end, a distal end, an elastic portion interposed the proximal end and the distal end, and a lumen therethrough. An anchor sleeve is disposed coaxially over the tubular member and has a radially expandable region. The anchor sleeve is moveable between an axially elongated configuration and an axially shortened configuration and is biased toward the axially shortened configuration by a force exerted by the elastic portion of the tubular member. The axially shortened configuration corresponds to the anchor sleeve being in the fully deployed position. Methods for providing anchored access to a cavity within a patient are also disclosed.

21 Claims, 8 Drawing Sheets

U.S. PATENT DOCUMENTS

| | | | |
|---|---|---|---|
| 4,641,634 A | 2/1987 | Storz | |
| 4,664,114 A | 5/1987 | Ghodsian | |
| 4,716,893 A | 1/1988 | Fischer et al. | |
| 4,721,103 A | 1/1988 | Freedland | |
| 4,779,612 A | 10/1988 | Kishi | |
| 4,820,270 A | 4/1989 | Hardcastle et al. | |
| 4,836,189 A | 6/1989 | Allred, III et al. | |
| 4,885,003 A | 12/1989 | Hillstead | |
| 4,911,148 A | 3/1990 | Sosnowski et al. | |
| 4,921,478 A | 5/1990 | Solano et al. | |
| 4,949,718 A | 8/1990 | Neuwirth et al. | |
| 4,984,564 A | 1/1991 | Yuen | |
| 5,002,557 A | 3/1991 | Hasson | |
| 5,041,093 A | 8/1991 | Chu | |
| 5,053,009 A | 10/1991 | Herzberg | |
| 5,073,166 A * | 12/1991 | Parks et al. | 604/175 |
| 5,073,169 A * | 12/1991 | Raiken | 604/180 |
| 5,104,377 A | 4/1992 | Levine | |
| 5,122,122 A | 6/1992 | Allgood | |
| 5,176,697 A | 1/1993 | Hasson et al. | |
| 5,188,602 A | 2/1993 | Nichols | |
| 5,209,754 A | 5/1993 | Ahluwalia | |
| 5,242,390 A | 9/1993 | Goldrath | |
| 5,259,836 A | 11/1993 | Thurmond et al. | |
| 5,263,922 A * | 11/1993 | Sova et al. | 602/59 |
| 5,267,970 A | 12/1993 | Chin et al. | |
| 5,344,439 A | 9/1994 | Otten | |
| 5,421,832 A | 6/1995 | Lefebvre | |
| 5,454,790 A | 10/1995 | Dubrul | |
| 5,540,658 A | 7/1996 | Evans et al. | |
| 5,695,517 A | 12/1997 | Marin et al. | |
| 5,741,234 A * | 4/1998 | Aboul-Hosn | 604/174 |
| 5,792,155 A | 8/1998 | Van Cleef | |
| 5,803,901 A | 9/1998 | Chin et al. | |
| 5,836,913 A * | 11/1998 | Orth et al. | 604/107 |
| 5,882,345 A | 3/1999 | Yoon | |
| 5,891,094 A | 4/1999 | Masterson et al. | |
| 5,944,730 A | 8/1999 | Nobles et al. | |
| 6,066,132 A | 5/2000 | Chen et al. | |
| 6,146,400 A | 11/2000 | Hahnen | |
| 6,171,319 B1 | 1/2001 | Nobles et al. | |
| 6,174,317 B1 | 1/2001 | Engman | |
| 6,228,068 B1 | 5/2001 | Yoon | |
| 6,231,588 B1 | 5/2001 | Zadno-Azizi | |
| 6,312,407 B1 | 11/2001 | Zadno-Azizi et al. | |
| 6,355,028 B2 | 3/2002 | Castaneda et al. | |
| 6,409,739 B1 | 6/2002 | Nobles et al. | |
| 6,464,690 B1 | 10/2002 | Castañeda et al. | |
| 6,464,691 B1 | 10/2002 | Castañeda et al. | |
| 6,482,178 B1 | 11/2002 | Andrews et al. | |
| 6,494,893 B2 | 12/2002 | Dubrul et al. | |
| 6,500,113 B2 | 12/2002 | Vilos | |
| 6,503,245 B2 | 1/2003 | Palmer et al. | |
| 6,511,469 B2 | 1/2003 | Ackerman et al. | |
| 6,551,303 B1 | 4/2003 | Van Tassel et al. | |
| 6,558,401 B1 | 5/2003 | Azizi | |
| 6,578,577 B2 * | 6/2003 | Bonadio et al. | 128/850 |
| 6,582,420 B2 | 6/2003 | Castañeda et al. | |
| 6,589,208 B2 | 7/2003 | Ewers et al. | |
| 6,592,573 B2 | 7/2003 | Castañeda et al. | |
| 6,607,504 B2 * | 8/2003 | Haarala et al. | 604/93.01 |
| 6,648,906 B2 | 11/2003 | Lasheras et al. | |
| 6,652,555 B1 | 11/2003 | Van Tassel et al. | |
| 6,652,556 B1 | 11/2003 | Van Tassel et al. | |
| 6,689,150 B1 | 2/2004 | Van Tassel et al. | |
| 6,692,462 B2 | 2/2004 | Mackenzie et al. | |
| 2003/0167069 A1 * | 9/2003 | Gonzales et al. | 606/200 |

FOREIGN PATENT DOCUMENTS

| | | |
|---|---|---|
| FR | 2810555 | 12/2001 |
| WO | WO 98/50104 A | 11/1998 |
| WO | WO 2004/028613 A2 | 4/2004 |

OTHER PUBLICATIONS

European Search Report for corresponding EP 09179213 date of mailing is Jan. 19, 2010 (3 pages).

* cited by examiner

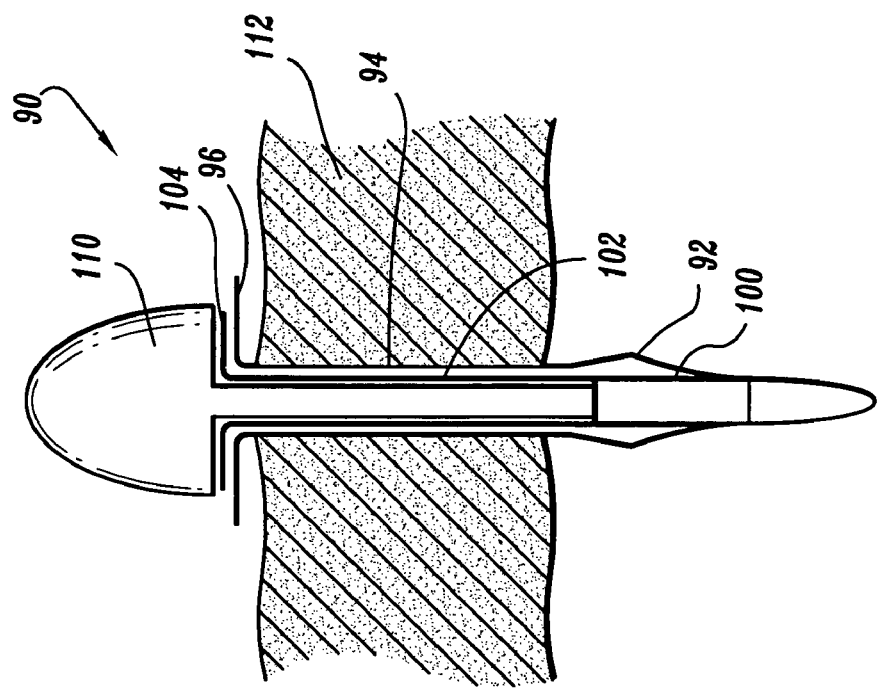
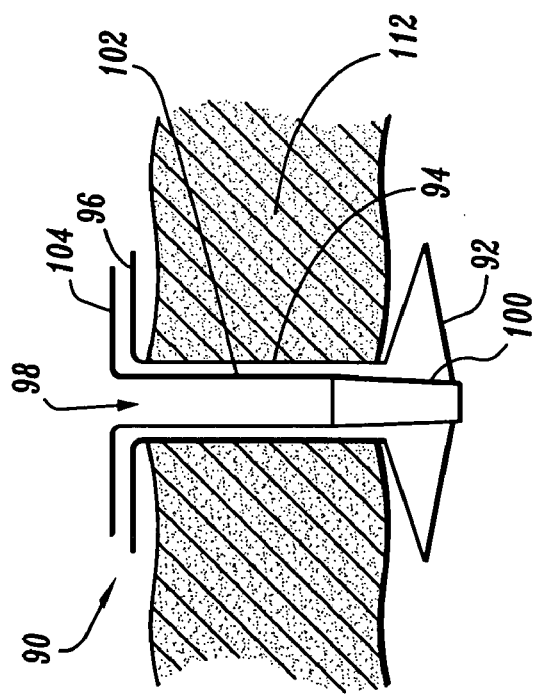

TROCAR ANCHOR

BACKGROUND

1. Technical Field

The present disclosure relates generally to apparatus and methods for accessing the interior of the body for performing surgery, diagnostics or other medical procedures. In particular, the present disclosure relates to an access assembly having an expandable anchor to secure and seal the access assembly to the patient's body.

2. Discussion of Related Art

Minimally invasive surgical procedures have recently been developed as alternatives to conventional open surgery. Minimally invasive procedures, such as laparoscopy, involve accessing the surgical area inside a patient through a plurality of ports introduced into the patient's body. This type of procedure is generally less traumatic to the body than open surgery, since these ports tend to cause less tissue damage and blood loss as compared to long incisions made for open surgery. A working space is typically created to provide space inside the surgical area for instruments to operate. For example, in laparoscopic surgery, the abdominal wall is elevated away from the organs in the body cavity. This is usually accomplished by filling the body cavity with a gas, such as carbon dioxide, raising the abdominal wall. This process, known as insufflation, is typically achieved by inserting a large-gauge needle known as a Veress needle into, for example, the intra-abdominal cavity for the introduction of gas. To perform surgical procedures in the intra-abdominal cavity, the insufflation pressure must be maintained, and the abdominal wall must remain elevated from the organs in the intra-abdominal cavity.

Once enlarged, the cavity may be accessed by inserting a trocar and cannula assembly through the abdominal wall. The trocar is a sharp stylet used to provide an initial penetration and access opening in the abdominal wall for the cannula. The trocar is removed and the cannula remains in the body to provide access to the surgical site.

In an alternative method known as the "open laparoscopy" method or the Hasson method, access is established to the peritoneal cavity through a small incision on the skin of the abdomen, typically through the umbilicus. A special open laparoscopic cannula is inserted. The physician uses standard laparotomy instruments and grasping forceps to laterally enlarge the initial incision and to lift/separate the fascia. This procedure eventually exposes the peritoneum and places it under tension so that it can be carefully pierced. Once accessed, the physician can pass a gloved finger into the cavity accessing the relevant anatomy and confirming safe entry. Upon securing access, the physician inserts the cannula through the incision and continues with a standard laparoscopic procedure.

During the surgical procedure, the pressurized integrity of the peritoneal cavity or pneumoperitoneum must be maintained even though there is substantial movement of the cannula during surgery. Unfortunately, it is often difficult to maintain a proper seal between the cannula and body tissue at the initial incision point. Prior art devices have typically employed a conical shaped sealing sleeve generally constructed from a rigid material. Upon insertion into the incision, the sleeve engages the tissue along the thickness of the incision and the sleeve's conical geometry pushes or displaces outward the tissue surrounding the incision. The tissue's natural resiliency will then cause the tissue to try to return to the tissue's original position which creates a sealing force against the surface of the sealing sleeve. The sleeve is usually sutured to the skin at a depth and position where the tissue's resiliency provides sufficient compression to maintain a seal. Another device maintains the integrity of the gas seal and anchors the cannula to the body using an inflatable membrane at the distal end of the cannula. A sealing member is pushed against the exterior side of the body, capturing tissue between the sealing member and the inflatable membrane.

It is also known to provide access for a surgeon to introduce his or her hand into the body during laparoscopic surgery. Such a hand access port should also be anchored to the patient's body, while providing a seal around the incision.

Accordingly, a need exists for apparatus and methods for anchoring a cannula or other access member to a patient with minimum tissue trauma while still providing a positive seal.

SUMMARY

The present disclosure is directed to apparatus and methods capable of providing a gas seal against a percutaneous opening in a patient without the use of suturing, external adhesive devices, or an inflatable anchor. The apparatus of the present disclosure generally has an expandable anchor designed to prevent withdrawal of a surgical access device such as a cannula while maintaining pneumoperitoneum in the cavity. The anchor is integrated into the device design, will not rupture, does not traumatize the body tissue against which it anchors, and automatically deploys following placement into the patient.

In one embodiment, the apparatus of the present disclosure is an access assembly having a tubular member having a proximal end, a distal end, an elastic portion interposed the proximal end and the distal end, and a lumen therethrough. An anchor sleeve is disposed coaxially over the tubular member and has a radially expandable region. The anchor sleeve is moveable between an axially elongated configuration and an axially shortened configuration and is biased toward the axially shortened configuration by a force exerted by the elastic portion of the tubular member. The axially shortened configuration corresponds to the anchor sleeve being in the fully deployed position. Thus, an external force must be applied to the anchor sleeve to overcome the force exerted by the elastic portion of the tubular member and place the anchor sleeve in the undeployed position for entry in or exit from a percutaneous opening.

A method of the present disclosure for providing access to a cavity in a patient includes the method step of introducing a tubular body through a percutaneous opening in the patient's dermis. A radially expandable member mounted on the tubular body is axially compressed to radially expand the member. This expansion provides a seal against the internal surface of a patient's dermis. The cavity is insufflated with a gas to provide space in the abdomen for surgical instruments. The seal created by the expandable region inhibits loss of the gas through the penetration. A proximal flange on the tubular body may be advanced to clamp against the exterior surface of the patient's dermis.

These and other embodiments of the present disclosure, as well as its advantages and features, are described in more detail in conjunction with the text below and attached figures. Advantageously, the present disclosure provides apparatus and methods for anchoring a cannula to a patient with minimum tissue trauma while still providing a positive seal.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

FIG. 8 is a cross-sectional view of an access assembly with an undeployed anchor having an obturator positioned within the anchor such that the obturator stretches the elastic tubing in accordance with the embodiment of FIG. 7; and FIG. 9 is a cross-sectional view of an access assembly with a deployed anchor in accordance with the embodiment of FIGS. 7 and 8.

DETAILED DESCRIPTION OF PREFERRED EMBODIMENTS

Figure 1:
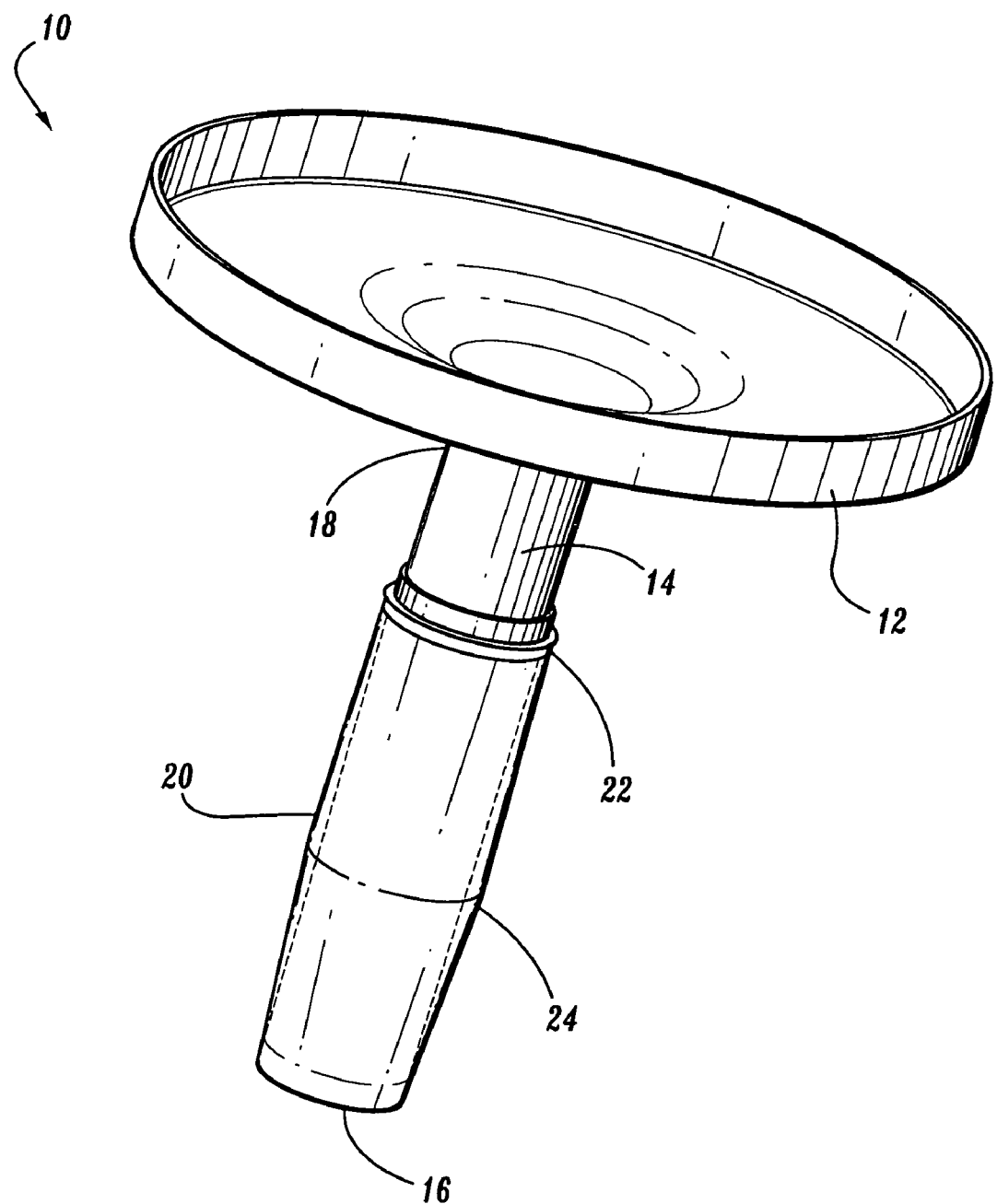
FIG. 1 illustrates a perspective view of the access assembly in accordance with an embodiment of the present disclosure.

Methods and apparatus of the present disclosure are directed towards providing access to a body cavity for surgical procedures. Specifically, methods and apparatus of the present disclosure substantially prevent substantial loss of insulation fluids through an incision by providing an access assembly that can form a peripheral seal against the incision and anchor the access assembly to the body, while allowing surgical instruments to access the interior of the body during minimally invasive surgical procedures.

To reach a desired body cavity, the access assembly is inserted through a percutaneous opening in the patient's body, such as an incision through the abdominal wall. The access assembly must typically pass through the abdominal wall which includes the outer skin, a layer of fat, a layer of fascia or alternating muscle and fascia, and the peritoneum. The layers of fat and fascia may vary in thickness, depending upon the body location and whether the patient is asthenic or obese. The peritoneum is a strong, elastic membrane lining the walls of the abdominal cavity. Just below the peritoneum, lie several vital organs, such as the liver, stomach and intestines, and other sensitive tissues. This is typically the area that the access assembly is positioned to reach.

To perform surgical procedures in this area, the abdominal wall is lifted off of the organs by inflating the area with an insufflation gas such as carbon dioxide. This provides sufficient space for surgical instruments to maneuver. To prevent loss of this gas and loss of working space, the access assembly must provide a gas-tight seal against the abdominal wall while permitting a sufficient range of motion for the instruments and minimizing damage to the portion of the abdominal wall engaged by the seal.

Although the present disclosure is described with reference to a surgical procedure which includes a penetration of the abdominal wall, such description is made for illustrative and exemplary purposes. As those skilled in the art will appreciate, many other surgical procedures may be performed by utilizing the methods and materials described herein. Preferred embodiments of the presently disclosed access assembly, anchor and methods of using the foregoing will now be described in detail with reference to the figures, in which like reference numerals identify corresponding elements throughout the several views. As used herein, the term mesh is intended to encompass a broad range of structural configurations including, but not limited to woven and non-woven structures, fabrics, weaves, braids, knits and/or felts.

Referring initially to FIG. 1, a perspective view of an access assembly in accordance with an embodiment of the present disclosure is illustrated. The access assembly 10 of the present disclosure generally comprises a hub member 12 having a blunt sheath tube 14 extending distally therefrom. An obturator or a trocar, slides removably into a lumen 16 defined by the sheath tube 14.

The hub member 12 may be fitted with a pneumostasis valve (not shown) on a proximal end for sealably receiving a surgical instrument therethrough. The pneumostasis valve may be housed inside hub member 12 or otherwise attached to the hub member 12 by means known to one having ordinary skill in the art. The valve may be a flap valve, a duckbill valve, or a gas-restricting device of some other design, so long as it allows entry of a surgical instrument while reducing the loss of insufflation gas during the surgical procedure. The pneumostasis valve prevents loss of gas by automatically closing access to the sheath tube 14 when surgical instruments are being switched. Desirably, a second valve for sealing around the instrument is provided for minimizing the loss of insufflation gas while an instrument is inserted through the access assembly.

The sheath tube 14 has an expandable region 24. The expandable region 24 comprises an anchor sleeve 20 disposed coaxially over the distal portion of sheath tube 14. The anchor sleeve 20 may be retained on sheath tube 14 by an anchor flange 22, or the anchor sleeve 20 may be attached to a distal end of sheath tube 14. For example, the anchor flange 22 is tightened around anchor sleeve 20 to compress the anchor sleeve against sheath tube 14 to hold the anchor sleeve 20 in place. The anchor sleeve 20 is illustrated in FIG. 1 in an undeployed position. As will be discussed in further detail below, the resting position for anchor sleeve 20 is the fully deployed position. An outside force is required to maintain anchor sleeve 20 in the undeployed position.

Figure 2:
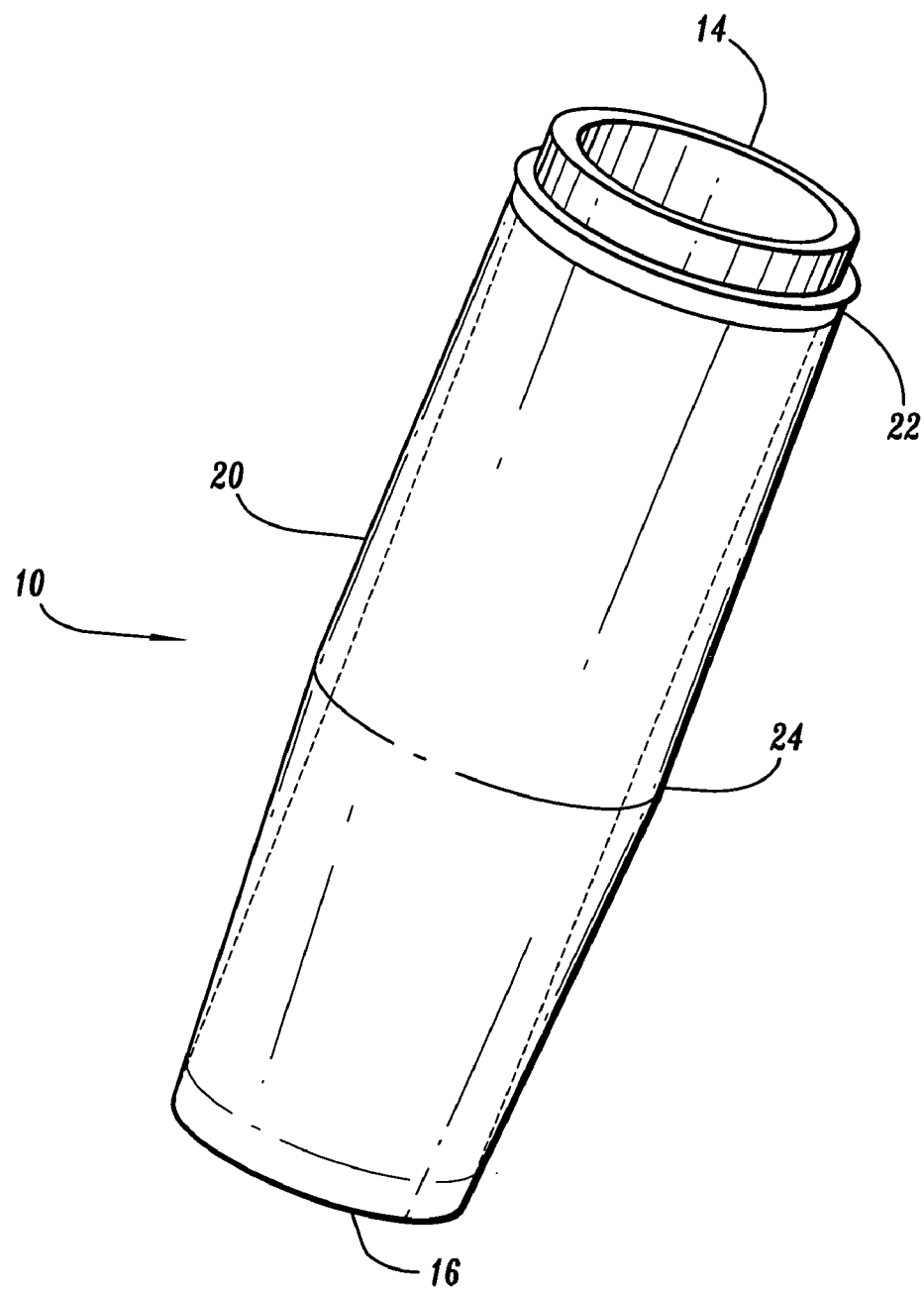
FIG. 2 illustrates a perspective view of the distal end of the access assembly in the undeployed position, in accordance with the embodiment of FIG. 1.
Figure 3:
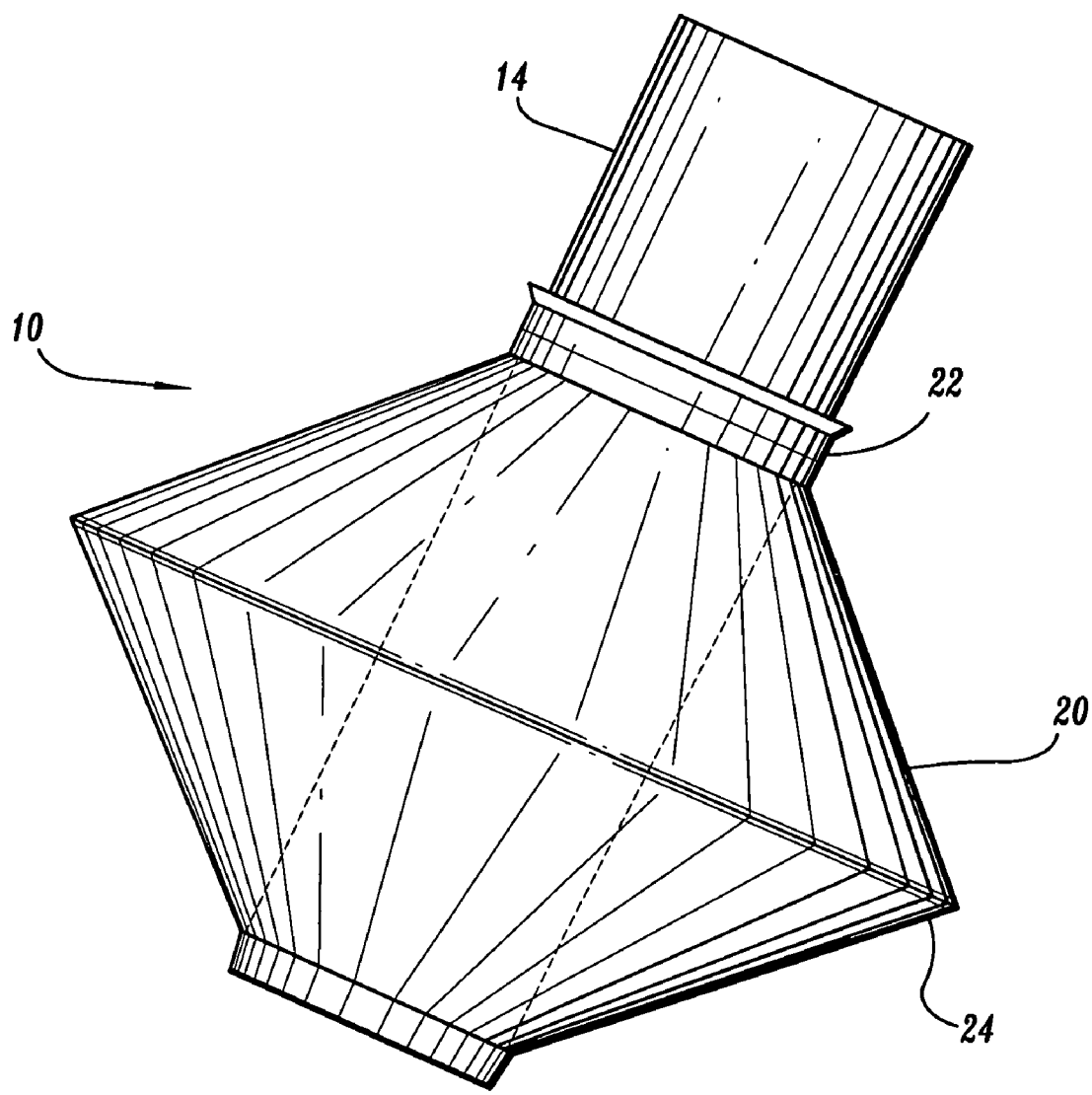
FIG. 3 illustrates a perspective view of the distal end of the access assembly in the partially deployed position, in accordance with the embodiment of FIGS. 1 and 2.
Figure 4:
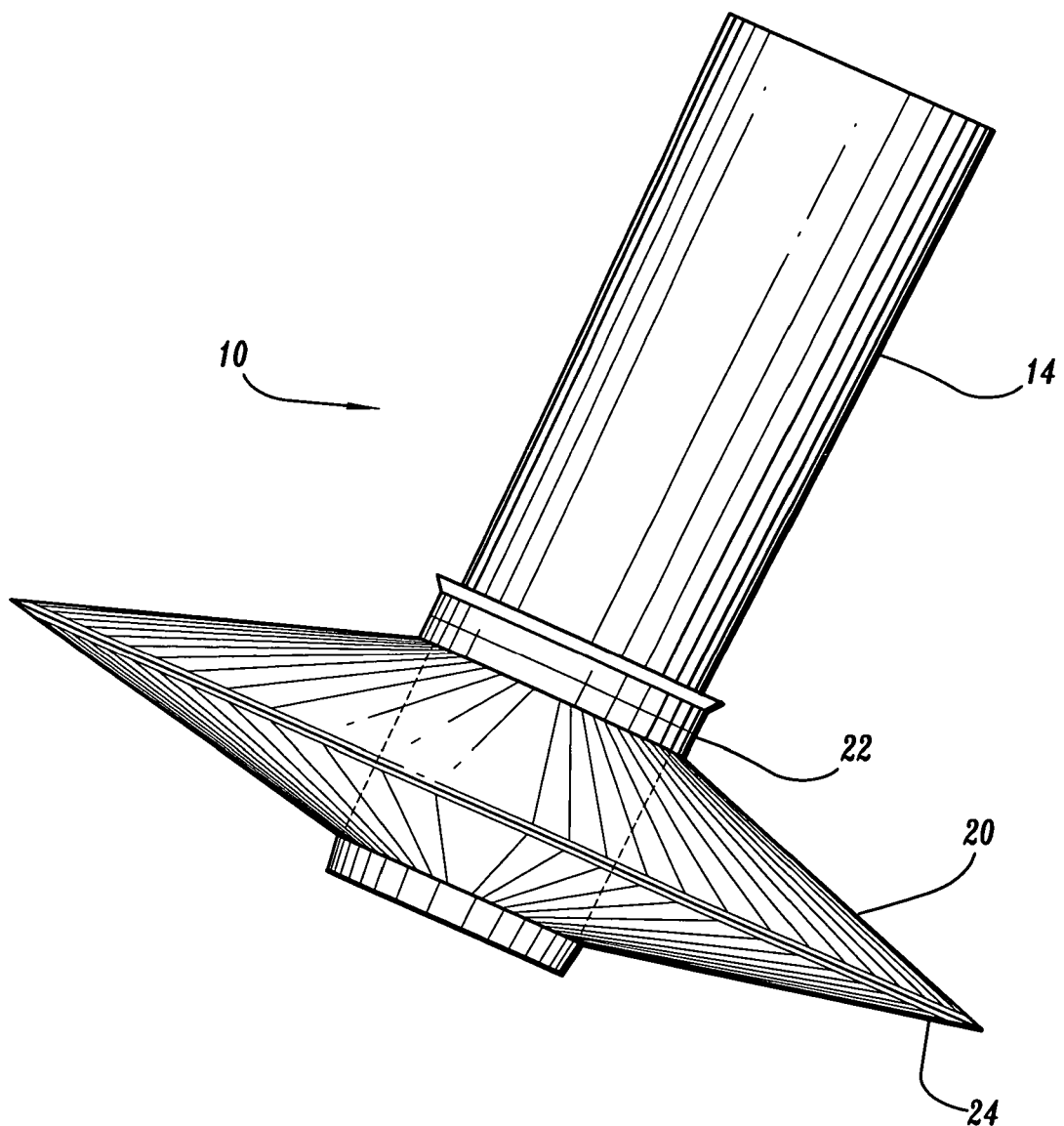
FIG. 4 illustrates a perspective view of the access assembly in the fully deployed position, in accordance with the embodiment of FIGS. 1-3.

FIG. 2 illustrates an isolated perspective view of the anchor sleeve 20 in the undeployed position, in accordance with the present disclosure. The anchor flange 22 is positioned around a proximal end of anchor sleeve 20 to compress the anchor sleeve against a sheath tube 14 to hold the anchor sleeve 20 in place. The anchor flange 22 is fitted around anchor sleeve 20 in a manner which will allow the proximal end of anchor sleeve 20 to slide distally along sheath tube 14. In that case, the anchor sleeve 20 is fixed around a circumference of sheath tube 14 at the distal end thereof. Thus, anchor sleeve 20 will expand to its normally biased deployed position, as illustrated in FIGS. 3 and 4. Alternatively, the proximal end of the anchor sleeve 20 may be fixed to sheath tube 14 and the distal end may be slidably held to sheath tube 14 by an anchor flange.

The prior art employs a variety of mechanisms, such as using a pistol grip advancing system or some other translating mechanism, to move and expand the anchor mechanism. The access assembly 10 in accordance with the present disclosure is automatically biased toward the expanded (deployed) position. Thus, when there is no external force holding the access assembly in the undeployed position, the access assembly 10 will return to the deployed position. For example, the access assembly may include a tube disposed around sheath tube 14 and having a distal end attached to the anchor flange 22. A latch at a proximal end of the assembly, holds the tube in a proximal-most position, retaining the anchor sleeve 20 in the undeployed position. Upon release of the latch, the anchor sleeve 20 moves to the deployed position.

In a further embodiment, the sheath tube 14 comprises a resilient and/or elastomeric material. The anchor flange 22 is attached to the sheath tube 14, without being slidable in the longitudinal direction. A trocar or obturator is arranged so as to engage the sheath tube 14, stretching the sheath tube in a longitudinal direction, when the trocar is inserted into the sheath tube 14. As the sheath tube 14 is stretched, the anchor sleeve 20 is elongated in the longitudinal direction, moving the anchor sleeve 20 to the undeployed position. Using the trocar, the distal end of the access assembly is then inserted into the body. Upon removal of the trocar, the anchor sleeve 20 returns to the deployed position.

The trocar, sheath tube 14, or both have structure for engaging the trocar with the sheath tube 14, when the trocar is inserted into the sheath tube 14. The trocar may have a flange or protrusion that engages a similar protrusion in the sheath tube 14. The sheath tube 14, trocar, or both may have a tapered shaped. The trocar and sheath tube 14 are arranged so that the trocar stretches the sheath tube 14, while permitting the cutting tip on the distal end of the trocar to protrude from the distal end of the sheath tube 14.

In a further embodiment, the anchor sleeve 20 is sufficiently flexible to collapse upon insertion in an incision. Thus, upon inserting the distal end of the access assembly into the body, the anchor sleeve 20 collapses. After the anchor sleeve 20 reaches the body cavity, the anchor sleeve 20 expands. Upon the removal of the access assembly from the body, the anchor sleeve 20 collapses, allowing removal with the application of a small proximally directed force.

FIGS. 3 and 4 illustrate progressive states of deployment of anchor sleeve 20. More specifically, FIG. 3 illustrates a perspective view of the anchor sleeve in the partially deployed position, in accordance with the present disclosure. FIG. 4 illustrates a perspective view of the anchor sleeve in the fully deployed position, in accordance with the present disclosure. As can be seen by analyzing FIGS. 2-4, as the anchor flange 22 moves distally, the anchor expands to form a peripheral seal between the access assembly 10 and a percutaneous opening in the abdominal wall. The anchor sleeve 20 comprises a flexible and/or elastic material and may comprise polymeric sheet materials, braided, woven, knitted and non-woven materials, and combinations thereof. The materials desirably comprise medical grade materials.

In a specific aspect of the present disclosure, the expandable region 24 is a non-distensible imperforate cylindrical surface preferably constructed from an elastomeric sheet covering a plurality of polymeric strands. Exemplary materials for the mesh material include braided polymer strands such as medical grade metals, PET, polypropylene, polyethylene, and the like. Exemplary materials for the elastomeric sheet include latex, silicone, thermoplastic elastomers (such as C-Flex, commercially available from Consolidated Polymer Technology), and the like. The braided material is braided in the shape of a cylinder, or otherwise formed into a cylindrical geometry, and, as mentioned, is translatably disposed over sheath tube 14.

The sheath tube 14 can be constructed from a variety of materials including stainless steel, composite filament wound polymer, or extruded polymer tubing (such as Nylon 11 or Ultem, commercially available from General Electric), and other materials known in the art. These materials have sufficient strength so that the sheath tube 14 will not collapse when inserted into the abdomen. Although specific dimensions vary depending on the surgical procedure, the sheath tube 14 typically has an outer diameter from about 4 mm to 20 mm and a length between about 5 cm and 15 cm.

Referring now to FIGS. 5A-5D, another embodiment of an access assembly 50 is disclosed. Access assembly 50 includes a sheath tube 54 and anchor sleeve 52. The sheath tube 54 is preferably configured to be self adjusting along its length. For example, sheath tube 54 may be of a telescoping design or it may be formed of an elastic material which will allow the sheath tube to stretch and contract in the longitudinal direction.

Figure 5A:
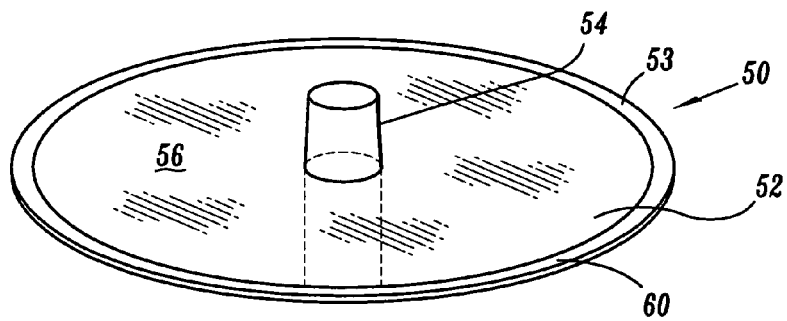
FIG. 5A is a perspective view of an access assembly in accordance with a further embodiment of the disclosure.

A short tip section of sheath tube 54 is illustrated in FIG. 5A. Prior to making the percutaneous opening in the patient, the anchor sleeve 52, which is made of a flexible and/or elastic material and may comprise the materials discussed above for anchor sleeve 20, is disposed on the patient's body and the sheath tube 54 extends proximally from the anchor sleeve 52. Once the percutaneous opening has been made, the sheath tube 54 is at least partially inserted into the opening.

An expandable region 56 of anchor sleeve 52 is preferably formed of an elastic membrane layer and a plurality of polymeric strands, such as the braided polymer strands of anchor sleeve 20. In a specific aspect of the present disclosure, the expandable region 56 is a non-distensible imperforate cylindrical surface preferably constructed from an elastomeric sheet covering the braided material. Exemplary materials for the braided material include polymer strands such as medical grade metals, PET, polypropylene, polyethylene, and the like. Exemplary materials for the elastomeric sheet include latex, silicone, thermoplastic elastomers (such as C-Flex, commercially available from Consolidated Polymer Technology), and the like. The braided material is braided in the shape of a cylinder or otherwise formed into a cylindrical shape and disposed over the sheath tube 54.

The anchor sleeve initially has the shape of a circular sheet. An outer member 53 is desirably attached to anchor sleeve 52 and is preferably formed of a relatively rigid material, as compared to the anchor sleeve 52, so as to hold the anchor sleeve 52 on the outer surface of the body. The outer member 53 may comprise an annular member 60 of at least semi-rigid material to assist in maintaining a circular configuration for anchor sleeve 52.

Figure 5B:
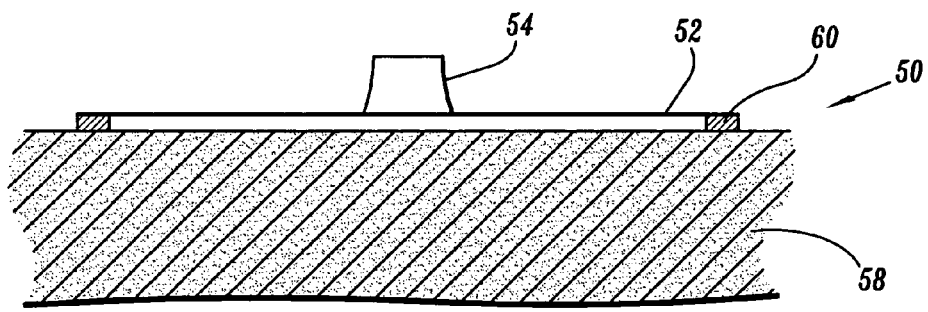
FIGS. 5B-D are cross-sectional views of an access assembly penetrating the tissue of a patient in accordance with the embodiment of FIG. 5A.
Figure 5C:
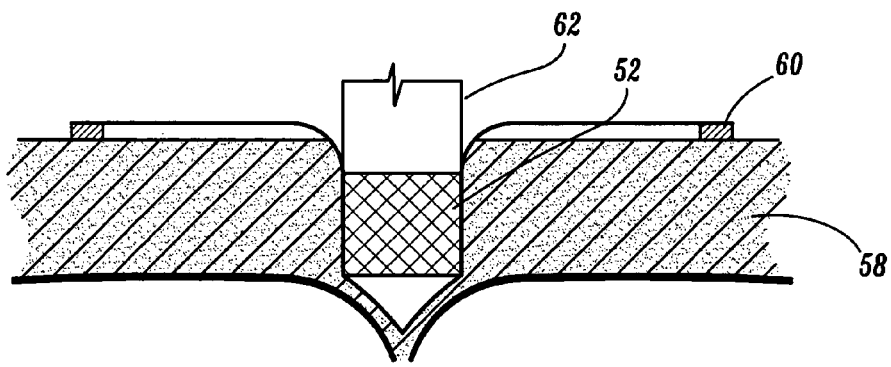
Figure 5D:
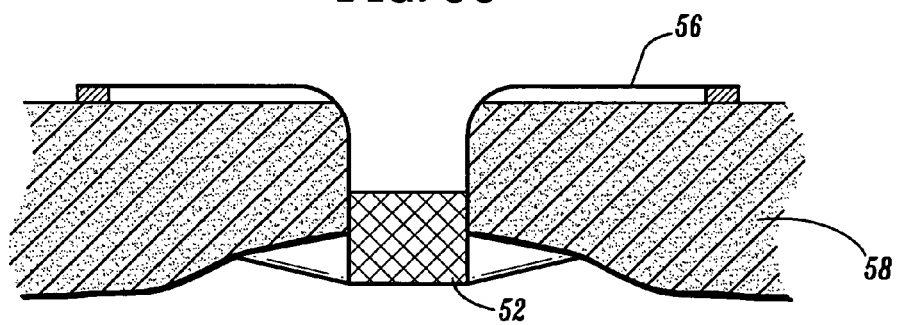

In use, and with continued reference to FIGS. 5A-D, the access assembly 50 is placed on the patient's body, as illustrated in FIG. 5B. In order to access the abdominal cavity, for example, a trocar device 62 is inserted into a proximal end of sheath tube 54. As discussed above, at rest, the access assembly 50 is in the fully deployed position, as illustrated in FIGS. 5A and 5B. Trocar device 62 is arranged such that, when it is inserted into a proximal end of the lumen defined by sheath tube 54, the trocar device engages the distal end of the sheath tube 54, thereby stretching the sheath tube 54 to a point where the anchor sleeve 52 collapses to a cylindrical shape with a diameter approximating the diameter of the trocar device 62. The trocar device 62 extends beyond the distal end of anchor sleeve 52 to form an opening in the skin of the patient. As illustrated in FIGS. 5C and 5D, a point or cutting edge of trocar device 62 extends beyond the distal end of the sheath tube 54 and anchor sleeve 52, so that the trocar device 62 penetrates the patient's skin and can advance into the underlying tissue of the abdominal wall. Once an opening is formed in the abdominal wall 58, trocar device 62 is removed from sheath tube 54. When the force of the trocar device 62, the sheath tube 54, which is holding anchor sleeve 52 in the undeployed position, retracts and anchor sleeve 52 returns to its deployed position. The opening in the abdominal wall holds the proximal end of the anchor sleeve 52, while allowing the anchor sleeve 52 to bulge outwardly at the distal end of the access assembly. Accordingly, in the deployed position, anchor sleeve 52 extends radially and exerts a force upon an inner surface of the patient's abdominal wall 58, thereby forming a seal which will prevent insufflation gas from escaping around the outer circumference of sheath tube 54.

To facilitate insertion of the access assembly into a preexisting percutaneous opening, a surgical instrument such as, preferably, a blunt obturator (not shown), is inserted into the sheath tube 54. A blunt obturator is preferred for the reason that it will tend to minimize the trauma to the location of the insertion of the access assembly through the percutaneous opening. As discussed above, at rest, the access assembly 50 is in the fully deployed position. Accordingly, a surgical instrument having a suitable diameter must be inserted into a proximal end of the lumen defined by sheath tube 54. Having a suitable diameter will permit the obturator to engage the distal end of anchor sleeve 52, thereby stretching the anchor sleeve to a point where the anchor sleeve 52 collapses to a cylindrical shape approximating the diameter of the blunt obturator. At this point, the access assembly 50 may be inserted through the percutaneous hole formed in the abdomen of the patient. Finally, the obturator is removed from the access assembly 50 and the anchor sleeve 52 will return to the fully deployed position, in response to the force of the sheath tube 54, thereby forming a peripheral seal against the inner surface of dermis 58 to prevent the loss of insufflation gas.

After the access assembly 50 is secured and peripherally sealed around the opening in the patient, the blunt obturator is completely removed from the sheath tube 54 so that surgical instruments (not shown) can be inserted into the lumen of sheath tube 54 to access the body cavity below.

In removing the access assembly 50 from the body, the anchor sleeve may be collapsible so that a small proximally-directed force can pull the access assembly 50 out of the incision. Alternatively or additionally, a trocar or blunt obturator may be used to stretch the sheath tube 54 and collapse the anchor sleeve.

Figure 6A:
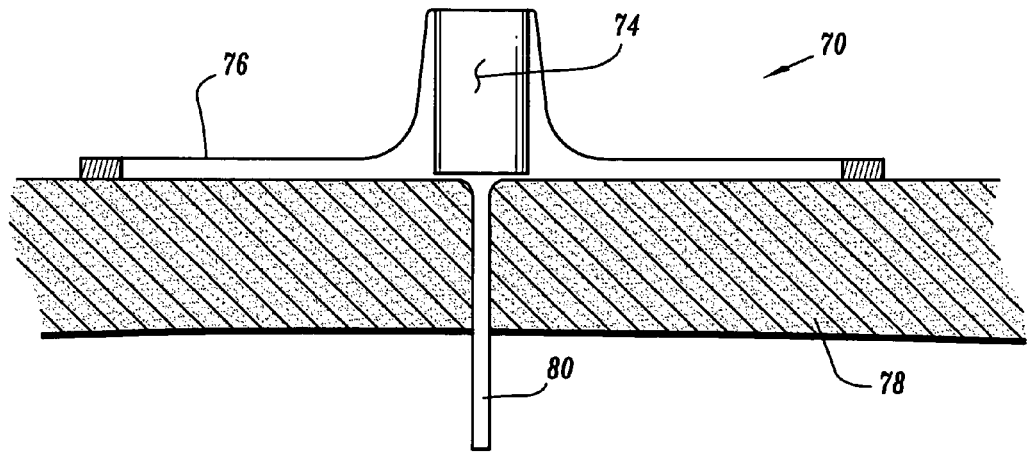
FIGS. 6A-B are cross-sectional views of an access assembly penetrating tissue in accordance with another embodiment of the present disclosure.
Figure 6B:
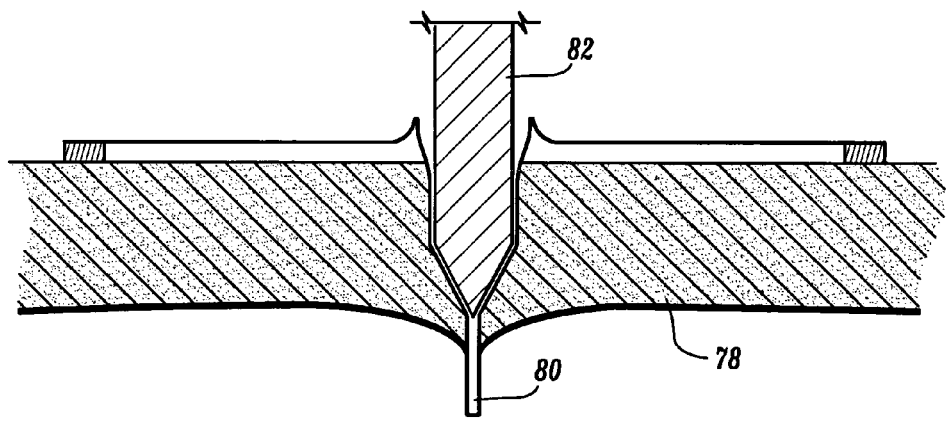

FIGS. 6A-D are side views of a trocar anchor penetrating the dermis layer of a patient in accordance with another embodiment of the present disclosure. This embodiment utilizes a step system to penetrate the dermis of the patient to allow the access assembly 70 to be inserted into the percutaneous opening. As the access assembly 70 is placed adjacent the dermis 78 of a patient, as illustrated in FIG. 6A, a tailpiece 80 of the access assembly 70 is inserted into the dermis 78 of the patient. The insertion of the tailpiece 80 into the dermis 78 provides stability to the remainder of the access assembly while also providing a pilot hole for the final percutaneous opening. Thus, the formation of the percutaneous opening and the insertion of an access assembly is achieved by a stepped approach.

Figure 6C:
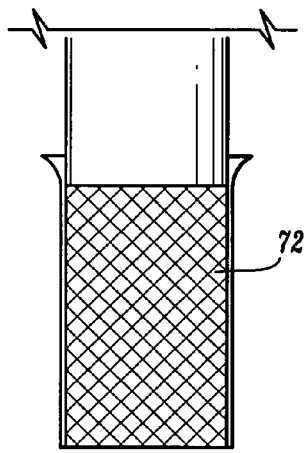
FIGS. 6C-D are side elevational views of the distal end of an access assembly in accordance with the embodiment of FIGS. 6A-B.
Figure 6D:
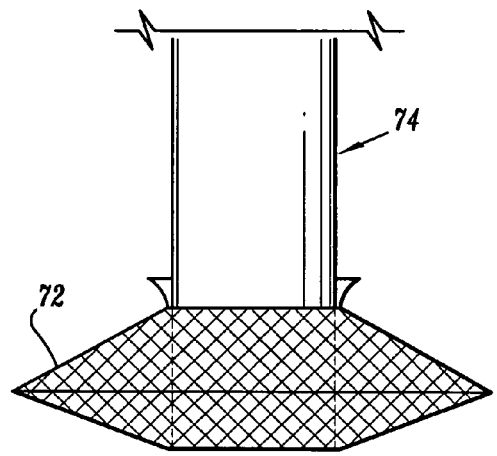

Once the tailpiece 80 has been inserted into the dermis 78, in order to form a percutaneous opening large enough to accommodate a surgical instrument, a trocar device 82 is inserted into a proximal end of sheath tube 74. As discussed above, at rest, the access assembly 70 is in the fully deployed position. Accordingly, trocar device 82 has a suitable diameter such that, when it is inserted into a proximal end of the lumen defined by sheath tube 74, the trocar device engages the distal end of anchor sleeve 72, thereby stretching the anchor sleeve 72 to a point where the anchor sleeve 72 collapses to its smallest diameter. The trocar device 82 then continues down through the pilot hole formed by tailpiece 80 to form an opening in the dermis 78 of the patient. As best illustrated in FIGS. 6C and 6D, once an opening is formed in the dermis 78, trocar device 82 is removed from sheath tube 74. When the force of the trocar device 82, which is holding anchor sleeve 72 in the undeployed position, as illustrated in FIG. 6C, is removed, anchor sleeve 72 returns to its biased, deployed position, as illustrated in FIG. 6D. In the deployed position, anchor sleeve 72 exerts a force upon an inner surface of dermis 78, thereby forming a seal which will prevent insufflation gas from escaping around the outer circumference of sheath tube 74.

Figure 7:
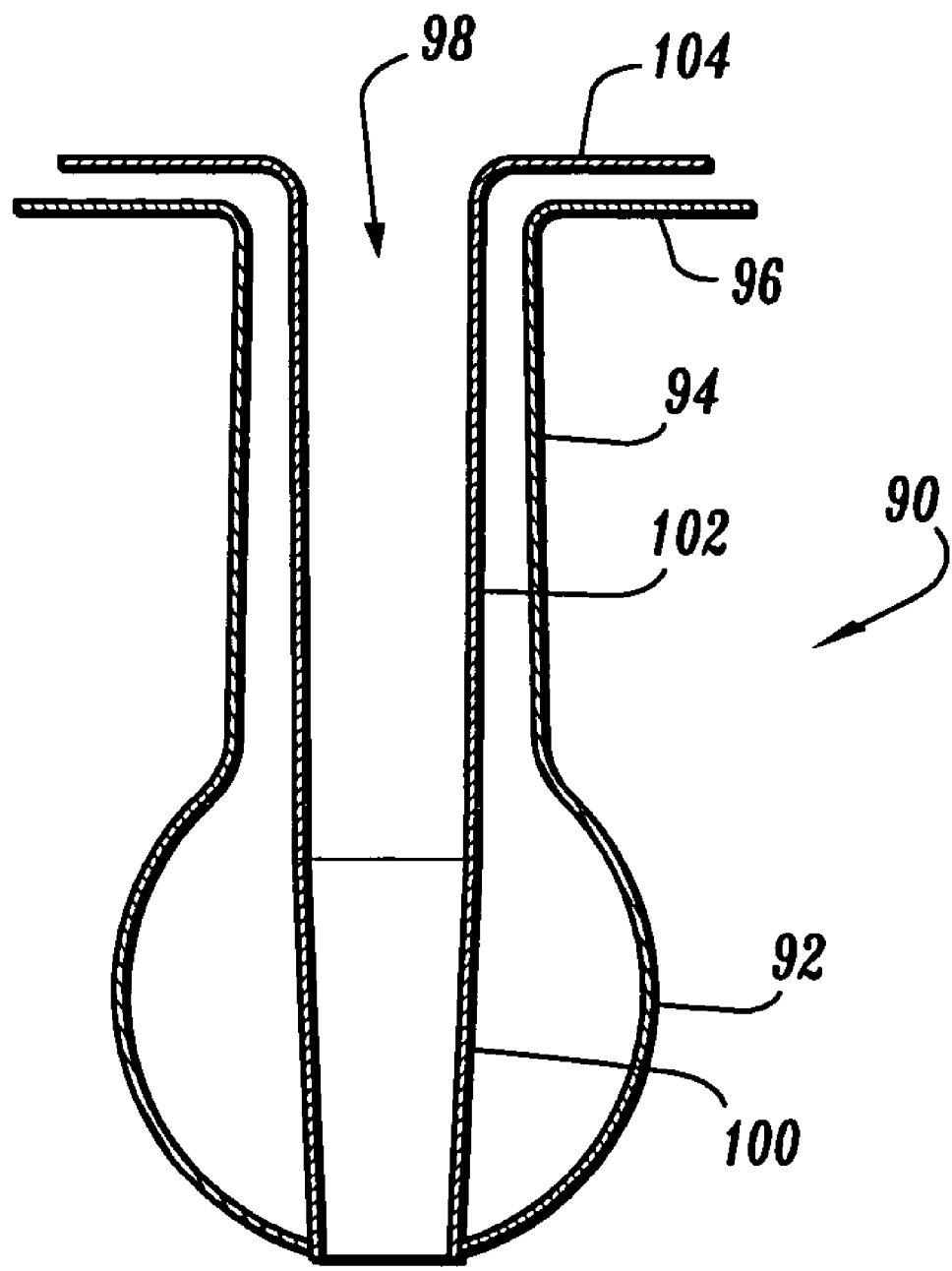
FIG. 7 is a cross-sectional view of an access assembly having a self adjusting sheath in accordance with a further embodiment of the present disclosure.

Referring now to FIG. 7, a side view of a trocar access assembly 90 having a self-adjusting sheath tube in accordance with another embodiment of the present disclosure is illustrated. The trocar access assembly 90 includes a anchor sleeve 92; an anchor base 94 which extends proximally from anchor sleeve 92; and an anchor flange 96 to prevent the access assembly from falling into the cavity of the patient. The anchor sleeve 92 is configured and dimensioned to form a peripheral seal around the percutaneous opening formed in the patient's body as it presses against the inner surface of the dermis of the patient. Similar to the embodiments described above, anchor sleeve 92 is predisposed to the deployed position by the self-adjusting sheath tube 98. An external force is required to alter the dimensions of anchor sleeve 92 such that anchor sleeve 92 is capable of being inserted into a percutaneous opening having a diameter which is less than the diameter of anchor sleeve 92 in the fully deployed position. Anchor flange 96 rests on an outer surface of the dermis of the patient around the periphery of the percutaneous opening.

A self-adjusting sheath tube 98 is disposed within trocar access assembly 90. Self-adjusting sheath tube 98 includes a tip portion 100, an elastic tubing portion 102, and a flange portion 104. Tip portion 100 forms the distal end of the self-adjusting sheath tube. Tip portion 100 is preferably formed of plastic. The elastic tubing portion 102 is connected at a distal end to the proximal end of the tip portion 100. Elastic tubing portion 102 forms the middle portion of the self-adjusting sheath tube 98. Flange portion 104 is connected to a proximal end of elastic tubing portion 102.

The distal end of anchor sleeve 92 is connected to a distal end of tip portion 100. Therefore, with reference to FIGS. 7 and 8, to insert the anchor sleeve 92 through a percutaneous opening in the dermis 112 of a patient, an obturator 110 or other instrument is inserted into the lumen defined by self-adjusting sheath tube 98. The obturator 110 is dimensioned such that it engages the distal end of tip portion 100. Upon further distal translation of the obturator 110, elastic tubing portion 102 elongates as a result of the force exerted by the obturator on tip portion 100. As tip portion 100 moves in the distal direction, anchor sleeve 92 is forced into the undeployed position, thereby forcing anchor sleeve 92 to have a smaller cross-section.

Once the trocar access assembly 90 is in position within the percutaneous opening formed in the dermis 112 of the patient, as illustrated in FIG. 8, obturator 110 is removed from the trocar access assembly 90 thereby allowing the elastic tubing portion 102 to return to its normal position. FIG. 9 illustrates the trocar access assembly 90 with the anchor sleeve 92 in the fully deployed position. Accordingly, in the deployed position, anchor sleeve 92 exerts a force upon an inner surface of dermis 112, thereby forming a seal which prevents insufflation gas from escaping around the outer circumference of sheath tube 98. Anchor flange 96 rests on an outer surface of dermis 112, to prevent the access assembly from falling into the cavity of the patient.

It will be understood that various modifications may be made to the embodiments disclosed herein. For example, although the above embodiments are described with reference to a surgical procedure implicating the abdomen, it is contemplated that the disclosure is not limited to such an application and may be applied to various medical instruments. Therefore, the above description should not be construed as limiting, but merely as exemplary of preferred embodiments. Those skilled in the art will envision other modifications within the scope and spirit of the claims.

What is claimed is:

1. A trocar access assembly for providing access to an internal worksite through an opening in tissue, the trocar access assembly comprising:
   an access member including an elastic anchor section and a self-adjusting sheath tube, the sheath tube being mounted to the anchor section and defining a lumen therethrough for reception of a surgical object, the sheath tube being movable between an initial position, where the sheath tube extends proximally from the anchor section and externally of the tissue, and an actuated position, where the sheath tube extends distally from the anchor section to be at least partially received within the opening in the tissue such that the sheath tube is at least partially positioned beneath the tissue, the anchor section being dimensioned and adapted to at least partially expand upon movement of the sheath tube to the actuated position to define an expanded segment adjacent the sheath tube, the expanded segment extending radially outwardly relative to the sheath tube and within the internal worksite to be in contacting engagement with internal tissue surfaces that form the opening, to thereby facilitate retention of the access member relative to the tissue.

2. The trocar access assembly as recited in claim 1 wherein the anchor section comprises a mesh material.

3. The trocar access assembly as recited in claim 1 wherein the sheath tube comprises a distal end and a proximal end defining a flange, the anchor section being interposed between the distal end and the proximal end.

4. The trocar access assembly as recited in claim 1 wherein the access member is connected to a distal end of the sheath tube.

5. The trocar access assembly as recited in claim 4 further comprising an obturator positionable within the lumen defined by the sheath tube, the obturator dimensioned to engage the distal end of the sheath tube and cause the sheath tube to transition from the initial position towards the actuated position during advancement within the lumen.

6. A surgical access assembly for providing access to an internal worksite through an opening in tissue, the surgical access assembly comprising:
   an access member including an elastic anchor section and a self-adjusting sheath tube, the sheath tube extending from the anchor section and defining a lumen therethrough configured and dimensioned to receive a surgical instrument, the access member being repositionable during use between an initial position, wherein the anchor section is configured and dimensioned for positioning adjacent an outer surface of a patient's tissue and the sheath tube extends proximally from the anchor section and externally of the tissue, and at least one subsequent position, wherein the sheath tube extends distally from the anchor section and beneath the tissue, wherein transitioning from the initial position to the at least one subsequent position creates a proximally directed biasing force in the anchor section whereby a contacting segment of the anchor section is defined, the contacting segment being configured and dimensioned to exert a proximally directed force on an inner surface of the tissue forming an opening to anchor the contacting portion and form a substantially fluid-tight seal between the self-adjusting sheath tube and the tissue.

7. The surgical access assembly of claim 6, wherein the anchor section is dimensioned to extend radially from the sheath tube.

8. The surgical access assembly of claim 7, wherein the anchor section extends in substantially perpendicular relation to the sheath tube when the access member is in the initial position.

9. The surgical access assembly of claim 6, wherein the sheath tube is adapted to contract radially inwardly during advancement of the surgical instrument therethrough such that an inner dimension of the sheath tube substantially approximates an outer dimension of the surgical instrument.

10. The surgical access assembly of claim 6, wherein the access member is biased towards the initial position.

11. The surgical access assembly of claim 6, wherein the anchor section includes a plurality of polymeric strands.

12. The surgical access assembly of claim 11, wherein the anchor section includes an elastomeric sheet positioned about the plurality of polymeric strands.

13. The surgical access assembly of claim 11, wherein the plurality of polymeric strands are constructed from materials selected from the group consisting of medical grade metals, PET, polypropylene, and polyethylene.

14. The surgical access assembly of claim 12, wherein the elastomeric sheet is constructed from materials selected from the group consisting of latex, silicone, and thermoplastic elastomers.

15. The surgical access assembly of claim 6 further including an outer member connected to a peripheral region of the anchor section.

16. The surgical access assembly of claim 15, wherein the outer member is formed from a material more rigid than the material comprising the anchor section such that the outer member maintains the anchor section externally of the patient's tissue.

17. An access assembly for providing access to an internal worksite through an opening in tissue, the access assembly comprising:
   an anchor section formed from a resilient material, the anchor section being configured and dimensioned for positioning adjacent an outer surface of the tissue;
   a self-adjusting sheath tube disposed concentrically within the anchor section and defining a lumen therethrough; and
   an obturator having proximal and distal ends and being removably positionable within the lumen of the sheath tube, the distal end of the obturator being engagable with a portion of the sheath tube whereby distal advancement of the obturator through the tissue facilitates expansion of the anchor section such that the anchor section is at least partially positioned within the opening and beneath the tissue such that the anchor section contacts internal tissue surfaces adjacent the opening to maintain positioning of the access assembly.

18. The access assembly of claim 17, wherein the sheath tube is adapted to transition between an initial position, in which the sheath tube is positioned proximally of the anchor section and externally of the tissue, and an actuated position, in which the sheath tube is positioned distally of the anchor section and at least partially beneath the tissue.

19. The access assembly of claim 18, wherein the anchor section is dimensioned and adapted to at least partially expand upon movement of the sheath tube to the actuated position to define an expanded segment adjacent the sheath tube, the expanded segment extending radially outwardly relative to the sheath tube and within the internal worksite to be in contacting engagement with the internal tissue surfaces that form the opening, to thereby facilitate retention of the access member relative to the tissue.

20. The access assembly of claim 19, wherein the sheath tube is biased toward the initial condition thereof whereby the expanded segment of the anchor section will be biased proximally toward the internal tissue surfaces adjacent the opening upon removal of the obturator.

21. The access assembly of claim 20, wherein the access member is sufficiently biased toward the initial condition whereby the expanded segment of the anchor section will establish a substantial sealed relation with the internal tissue surfaces adjacent the opening.

* * * * *